(12) United States Patent
Hubbard, Jr.

(10) Patent No.: US 6,678,550 B2
(45) Date of Patent: *Jan. 13, 2004

(54) MULTI ELECTRODE AND NEEDLE INJECTION DEVICE FOR DIAGNOSIS AND TREATMENT OF MUSCLE INJURY AND PAIN

(75) Inventor: David R. Hubbard, Jr., San Diego, CA (US)

(73) Assignee: Myolink, LLC, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/017,072

(22) Filed: Dec. 7, 2001

(65) Prior Publication Data

US 2002/0042590 A1 Apr. 11, 2002

Related U.S. Application Data

(63) Continuation of application No. 08/975,199, filed on Nov. 20, 1997, now Pat. No. 6,356,783.

(51) Int. Cl.[7] ................................................. A61B 5/04
(52) U.S. Cl. ........................................ 600/546; 604/187
(58) Field of Search ........................... 600/546, 548, 600/573–584, 587; 604/20, 21, 181, 187; 607/46

(56) References Cited

U.S. PATENT DOCUMENTS

| | | | |
|---|---|---|---|
| 3,313,293 A | * | 4/1967 | Chesebrough et al. ...... 600/373 |
| 3,682,162 A | * | 8/1972 | Colyer ........................ 600/373 |
| 4,016,870 A | | 4/1977 | Lock |
| 4,816,813 A | | 3/1989 | Furno et al. |
| 4,932,936 A | | 6/1990 | Dykstra et al. |
| 5,273,525 A | * | 12/1993 | Hofmann ..................... 604/21 |
| 5,306,236 A | * | 4/1994 | Blumenfeld et al. .......... 604/21 |
| 5,389,069 A | * | 2/1995 | Weaver ....................... 604/21 |
| 5,513,661 A | | 5/1996 | Hubbard |
| 5,593,429 A | | 1/1997 | Ruff |
| 5,599,346 A | | 2/1997 | Edwards et al. |
| 5,702,359 A | | 12/1997 | Hofmann et al. |
| 5,830,151 A | * | 11/1998 | Hadzic et al. ............... 600/554 |
| 6,009,875 A | | 1/2000 | Hubbard, Jr. |
| 6,280,604 B1 | * | 8/2001 | Allen et al. ............... 205/777.5 |
| 6,356,783 B1 | * | 3/2002 | Hubbard, Jr. ............... 600/546 |

FOREIGN PATENT DOCUMENTS

| | | | |
|---|---|---|---|
| WO | WO 95/10275 A1 | | 4/1995 |
| WO | WO 98/22021 A1 | | 5/1998 |

* cited by examiner

Primary Examiner—Charles Marmor
(74) Attorney, Agent, or Firm—Bradford J. Duft; James W. Collett

(57) ABSTRACT

A multi electrode and needle injection device for identifying and treating muscle pain using two simultaneous electrode EMG recordings to locate an active trigger point. The two electrodes are displaced so that one electrode detects EMG activity at the trigger point and the other detects EMG activity adjacent to the trigger point, within the same muscle. The combination of the electrodes with a drug delivery system allows the user to inject a medication locally at the trigger point to block the trigger point activity and reduce or eliminate muscle pain. The electrodes are on a hypodermic needle. The needle is used to both facilitate the location of the trigger points, and for treatment, by injecting a drug into the trigger points.

36 Claims, 5 Drawing Sheets

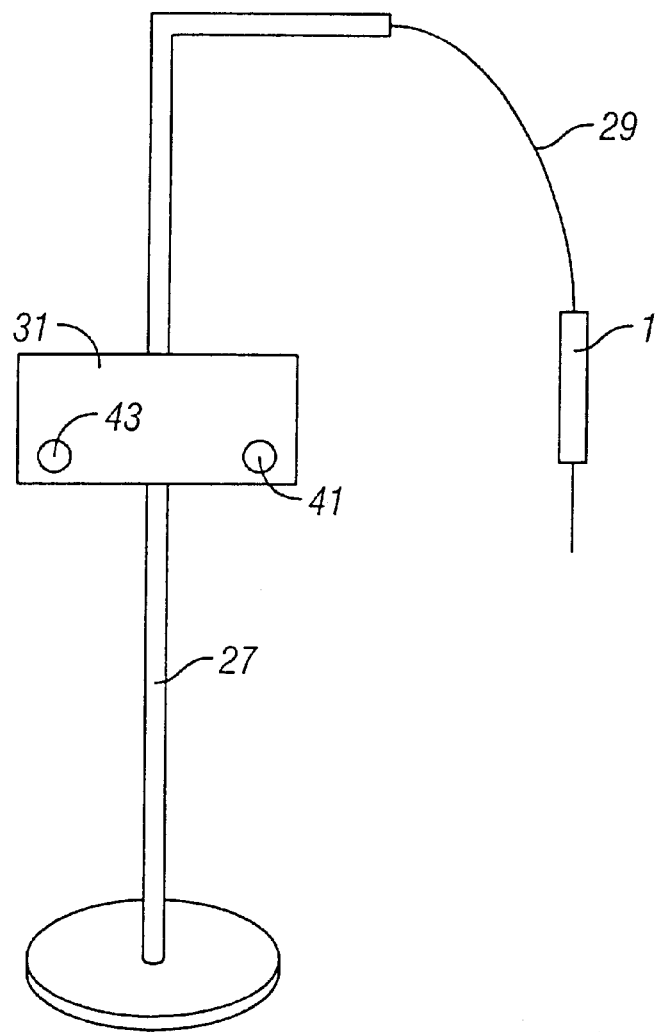
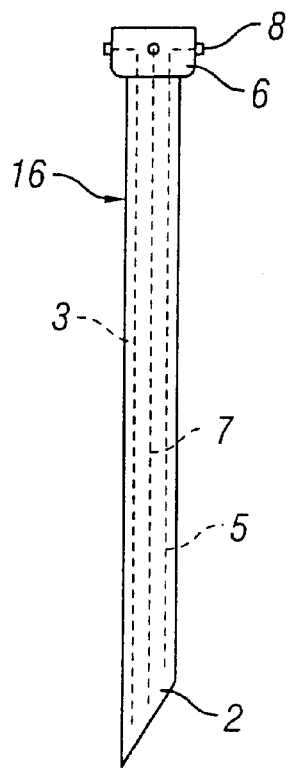
FIG. 5
FIG. 6

MULTI ELECTRODE AND NEEDLE INJECTION DEVICE FOR DIAGNOSIS AND TREATMENT OF MUSCLE INJURY AND PAIN

This application is a continuation application of U.S. application Ser. No. 08/975,199, filed Nov. 20, 1997, which has issued as U.S. Pat. No. 6,356,783.

BACKGROUND OF THE INVENTION

The field of the invention is the diagnosis and treatment of muscle injuries associated with pain and stiffness.

It is estimated that up to 20% of the adult population in the United States suffers from chronic and recurrent muscle pain. There is currently no FDA-approved or proven effective treatment for these conditions. Treatments now used give only limited temporary relief.

Chronic and recurring muscle pain is a neuromuscular abnormality typically following a strain injury, and manifested by what has been termed trigger point (TrP) phenomena. As used herein, trigger point means a localized area of tenderness within a muscle associated with spontaneous electromyographic (EMG) activity. Thus, a trigger point is a location of spontaneous EMG activity within a muscle associated with pain. Trigger points may be within muscle spindles. TrPs can be objectively diagnosed by identification of spontaneous EMG activity in a trigger point while adjacent muscle fibers are electromyographically quiet. Once the trigger point EMG activity is identified, chronic and recurrent muscle pain associated with this localized EMG activity can be treated through the use of medications including sympathetic blocking agents, as described in U.S. Pat. No. 5,513,661, incorporated herein by reference. This patent describes a method of identifying trigger points in muscle associated with a characteristic spontaneous EMG activity. The activity is then blocked by injecting adrenergic blocking agents. The methods of diagnosis and treatment described in U.S. Pat. No. 5,513,661 involves simultaneously measuring both the trigger point activity and the EMG activity adjacent to the trigger point to determine whether the observed trigger point EMG activity is spontaneous localized, and not due to other phenomena such as voluntary contraction. To effectively block sympathetic activity at a trigger point, it is desirable to localize the trigger point as precisely as possible. For effective treatment, the blocking agent should be delivered precisely at the trigger point. Accordingly, there remains a need for a device for simultaneously locating and treating TrP EMG activity.

SUMMARY OF THE INVENTION

To these ends, in a first aspect of the invention, an EMG device for diagnosing chronic and recurrent muscle pain preferably integrates two or more active EMG electrodes and an EMG reference electrode.

In a second aspect of the invention, an EMG device for treating chronic and recurrent muscle pain integrates two or more active EMG electrodes and a reference electrode and includes a drug delivery system.

In a third aspect of the invention, a system is provided for analyzing the level of spontaneous EMG activity in trigger points and adjacent muscle tissue.

Other objects and advantages will appear as well hereinafter.

BRIEF DESCRIPTION OF THE DRAWINGS

In the drawings, wherein similar reference characters denote similar elements, throughout the several views:

FIG. 5 is a schematically illustrated view of a trigger point analyzer, as used with an EMG Needle-Injection device;

FIG. 6 is a schematically illustrated view of the needle shown in FIG. 1; and

DETAILED DESCRIPTION OF THE PREFERRED EMBODIMENTS

In a first aspect of the invention, two or more active EMG electrodes and a reference electrode provide the ability to simultaneously show EMG activity at a trigger point, when adjacent muscle tissue EMG activity is relatively silent. The active electrodes are advantageously spaced apart to avoid having both electrodes sense the same EMG activity. The active electrodes, although spaced apart, are placed in the same muscle. The electrodes are used to locate a trigger point within a muscle. As described in U.S. Pat. No. 5,513,661, when a trigger point electrode shows active EMG activity, and an adjacent electrode is quiet (indicating the muscle is not contracting), a trigger point has been located. While use of electrodes and cables or wires is contemplated, a fully or partly wireless system maybe used, e.g., EMG with HP, infrared, or other wireless link between the sensors and an analyzer. Electrodes, as used here, includes those specifically shown and described, the various known conventional electrodes, as well as all other devices or systems for detecting EMG activity within a muscle.

Figure 1:
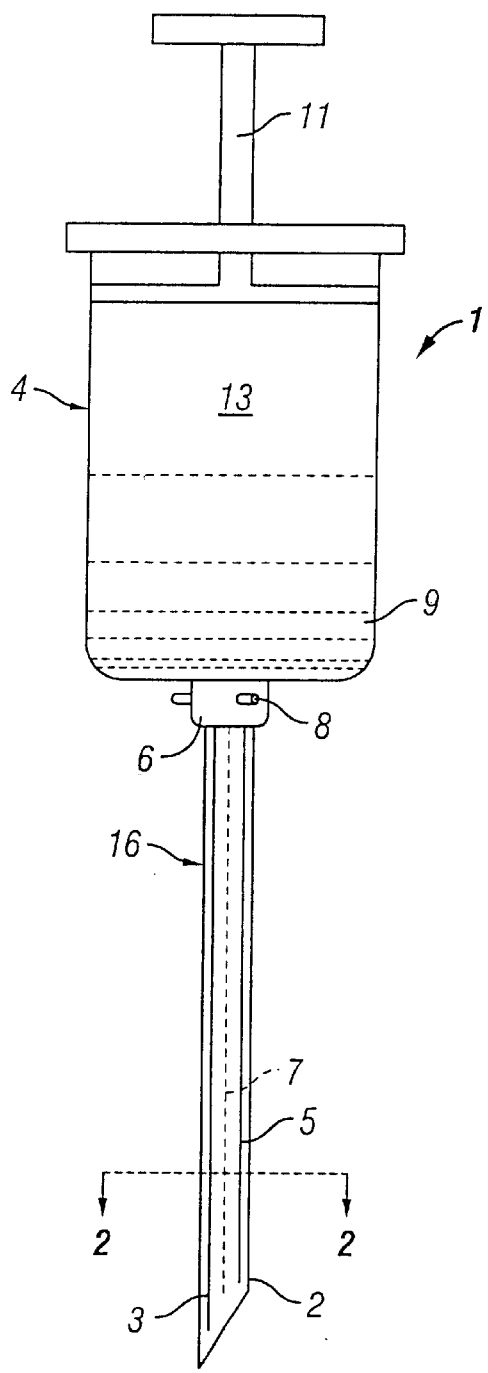
FIG. 1 is a front elevation view of an EMG needle-injection device according to a first embodiment.

Referring to FIG. 1, the device 1 has needle/electrode unit 16 including a hypodermic needle 2 with a sharp tip for insertion into a patient. The needle/electrode unit 16 is connected to a syringe 4 which contains a drug 13. The needle/electrode unit 16 has a hub 6 for connection to the syringe 4. The syringe 4 includes a drug containing vessel or ampoule, and a plunger 11 for containing and dispensing the drug. Various vessels or drug containers may be used in place of a conventional syringe. The needle and syringe are preferably disposable. The syringe body holds enough drug for one or preferably multiple doses. The drug may be phenoxybenzamine, phentolamine, an $\alpha$ agonist, an $\alpha_2$ agonist, guanethidine or other sympathetic blockers, or a local anesthetic such as lidocaine, or a neuro-muscular blocking agent such as Botulinutn Toxin Type A. Other therapeutically effective drugs may of course also be used. For the treatment of muscle pain, for example back muscle pain, the preferred drug is phenoxybenzamine.

In the embodiment of FIG. 1, three electrodes, 3, 5 and 7, are provided on the outside wall of the hypodermic needle 2. Preferably, the electrode 3 is a trigger point electrode for identifying the trigger point EMG activity of the afflicted muscle. The electrode 5 advantageously is an adjacent electrode for identifying the muscle tissue adjacent to and in the same muscle as the trigger point. Preferably, the electrode 7 is a reference electrode, used to provide a common reference voltage for the other two electrodes 3 and 5. While shown as round in cross section in FIG. 2, the electrodes may of course have other shapes or arrangements, or may be integral (e.g., etched into surfaces) of the needle.

Figure 2:
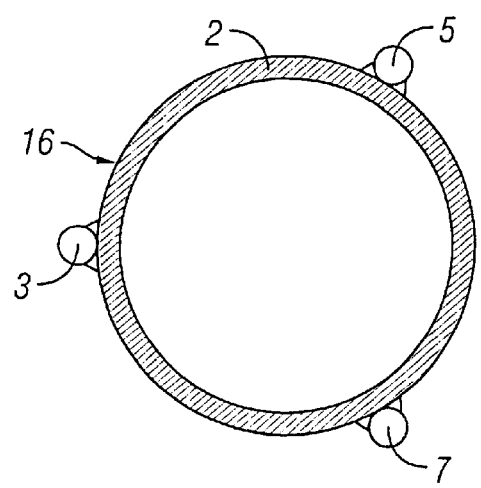
FIG. 2 is a section view taken along line 2—2 of FIG. 1.

All three electrodes are preferably made of a fine wire or other conductive material and are secured along the length of the hypodermic needle 2 outer wall as shown in FIG. 2. The electrodes 3, 5 and 7 are preferably insulated along their lengths, except for a small portion at their lower ends. The uninsulated portion of each electrode is the electrode's electrical contact, which is exposed to the patient's muscle tissue. The uninsulated portion of each electrode is positioned to avoid contacting the hypodermic needle 2 to prevent short-circuiting. As only a small section of each electrode is exposed, electrical measurements can be made at specific sites within a muscle. In a preferred embodiment, electrical connections 8 on the hub 6 provide for electrical connection to Clectromyography (EMG) equipment, such as an oscilloscope or computer monitor.

The electrical contacts of the trigger point electrode 3 and adjacent muscle electrode 5 are displaced from one another to enable the adjacent muscle electrode 5 to electrically contact the muscle fibers, in the same muscle, away from the trigger point area, and to prevent the electrode 5 from being exposed to any spontaneous EMG activity experienced at the trigger point. Typically, the trigger point electrode and the adjacent muscle electrode are spaced apart by about 1–8 mm and preferably by about 2–4 mm. The reference electrode 7 may be located vertically in between electrodes 3 and 5, as shown in FIG. 1, or further up the needle shaft, above electrode 5. The reference electrode 7 may alternatively be separate from the needle 2. The needle/electrode unit 16 may be provided separately from the drug containing vessel, as shown in FIG. 6. The separate needle/electrode unit 16 allows different size vessels to be selected and attached to the needle, and also allows the needle/electrode unit 16 to be reused if desired, after the vessel is empty. The needle/electrode unit 16 and vessel may be joined using Luer fittings or other known techniques.

By monitoring the EMG activity of the adjacent muscle electrode 5 and ensuring that it remains electrically silent, the clinician can verify that any EMG activity measured at the trigger point is localized and is not due to voluntary muscle contraction or other generalized contractions (e.g. involuntary splinting or bracing). EMG activity is determined by measuring the electrical potential of the trigger point electrode 3 and adjacent muscle electrode 5, referenced to the reference electrode 7. In this way the adjacent muscle electrode 5 serves as a control, which ensures the specificity of the trigger point electrode EMG readings. In this preferred embodiment, the electrical contacts of the trigger point electrode 3 and adjacent muscle electrode 5 are vertically spaced apart from one another. This allows the electrodes to be attached to a single hypodermic needle, thereby increasing ease of use, disposability and patient comfort. However, the electrodes may be horizontally spaced apart in other embodiments.

In use, the clinician manually palpates the affected muscle to find a trigger point as described in U.S. Pat. No. 5,513,661, noting local tenderness and the referral pattern of pain experienced by the patient when pressure is applied to the trigger point. The device 1 is connected to an EMG monitor, such that the trigger point electrode 3 and adjacent muscle electrode 5 are both referenced to the reference electrode 7. The clinician or physician then inserts the needle-electrode combination over the trigger point, slowly advancing it until the localized EMG activity at the trigger point is detected by the trigger point electrode 3, while the level of EMG activity from the adjacent electrode 5 remains relatively quiet. If both electrodes 3 and 5 detect significant EMG activity, the muscle is in a contracted condition and no diagnosis or treatment is made. In this situation, the patient is advised to relax the muscle, in an effort to obtain a better reading. If the adjacent electrode 5 shows relatively quiet EMG activity, while the trigger point electrode 3 shows active EMG activity, treatment with medication including sympathetic blocking agents is indicated. Preferably, amplitude and frequency values for the EMG activity are calculated and compared against pre-determined values.

The EMG device 1 may be used with an EMG analyzer 31 as shown in FIG. 5. In this embodiment, the analyzer 31 can be positioned on a stand or cart 27, and is joined to the device via a cable 29. The EMG analyzer 31 is designed to receive multiple electrical signals from the EMG needle-injection device 1 and continuously compute, display and store values for those signals. The analyzer preferably displays the electrical signals on a CRT or other display 41 and also optionally prints out hard copies of those signals.

The EMG analyzer 31 may also provide an audible or visual indication to the clinician when sustained EMG activity is occurring at the trigger point and not at the adjacent electrode 5. This can be done using known filtering or analogue-digital conversion and processing to determine when adjacent muscle activity is below a pre-determined level, for example, 13 microvolts (root mean square), and trigger point electrode activity is above a certain level, for example 26 microvolts (root mean square). Depending upon conditions, a difference of about 2:1 or more in EMG activity between a trigger point and the adjacent muscle, indicates a trigger point has been located and treatment by injection is appropriate.

Above threshold activity on the adjacent electrode could be signalled with, for example a steady high-pitched sound from a speaker 43 which would inform the clinician and the patient to relax the patient's muscles. EMG activity in the trigger point electrode could be amplified as a raw voltage signal which would inform the physician that he or she was near (for example within 1–4 mm) of the trigger point and would increase in amplitude as the electrode was further advanced into the trigger point.

Figure 3:
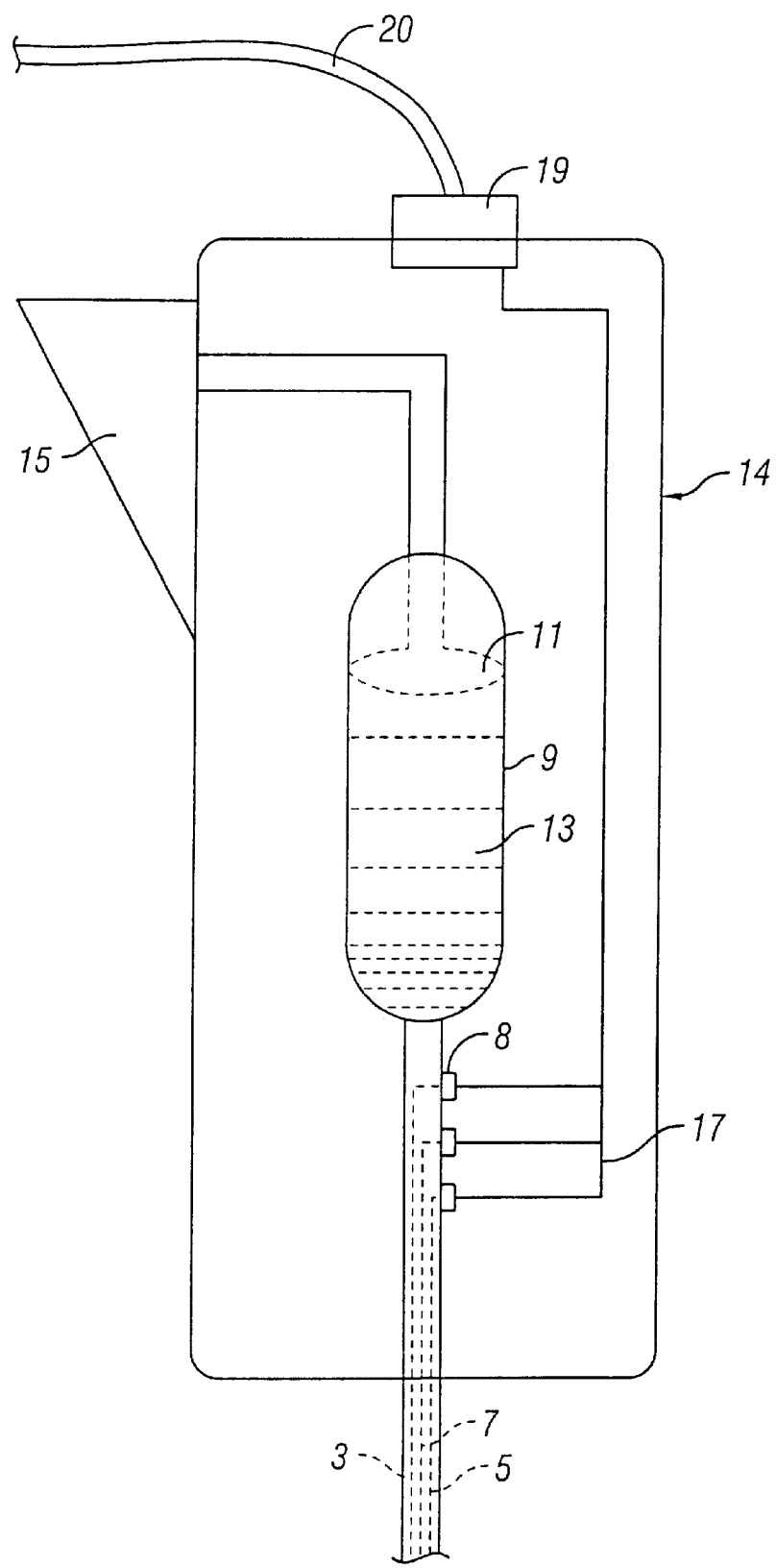
FIG. 3 is a schematically illustrated view of an EMG needle-injection device with a holder according to a second embodiment.

In a second preferred embodiment, as shown in FIG. 3, the preferably disposable EMG needle-injection device is used with a reusable holder 14. The holder 14, vessel 9 and plunger 11 all cooperate to form a drug delivery system. The holder accommodates the disposable EMG needle-injection device 1 and holds the device in place. The holder includes a thumb press 15, which acts on the plunger 11, to inject a fixed dosage of drug 13 into the patient. One or more doses, e.g., 5–20 or more doses, may be given from a single disposable EMG device. Alternatively, the dosage may be delivered via an electrically, mechanically or pneumatically powered device associated with or on or in the holder. A holder-needle connector 17 provides electrical connection between the needle electrode connectors 8 and an EMG electrical connector 19 on the holder. The EMG electrical connector 19 connects to an EMG measuring instrument or physiological monitor, such as an oscilloscope via a cable 20.

Preferably, the holder 14 has front and back sections joined at flex or hinge joint and a latch to hold the sections together. The interior of the holder 14 preferably has a recess shaped to receive and position the device 1. The holder-needle connector is positioned within the holder to automatically make contact with the connectors 8 when the holder is closed and latched. The thumb press 15 also automatically aligns with the plunger when the device is seated within the holder 14.

The holder 14 is a hand-held device which allows the user to deliver a fixed dosage of drug 13 to the patient while securing the electrode electrical connections, to minimize interference with the physician's examination. The injection device can be quickly removed from the holder, after use, and disposed of, and replaced with a new device. The holder therefore simplifies and expedites patient treatment. The circuitry and features of the analyzer may be miniaturized and included in the holder, eliminating the need for cables and a separate analyzer. The EMG signals may be processed by a microchip on or at the electrodes.

Figure 4:
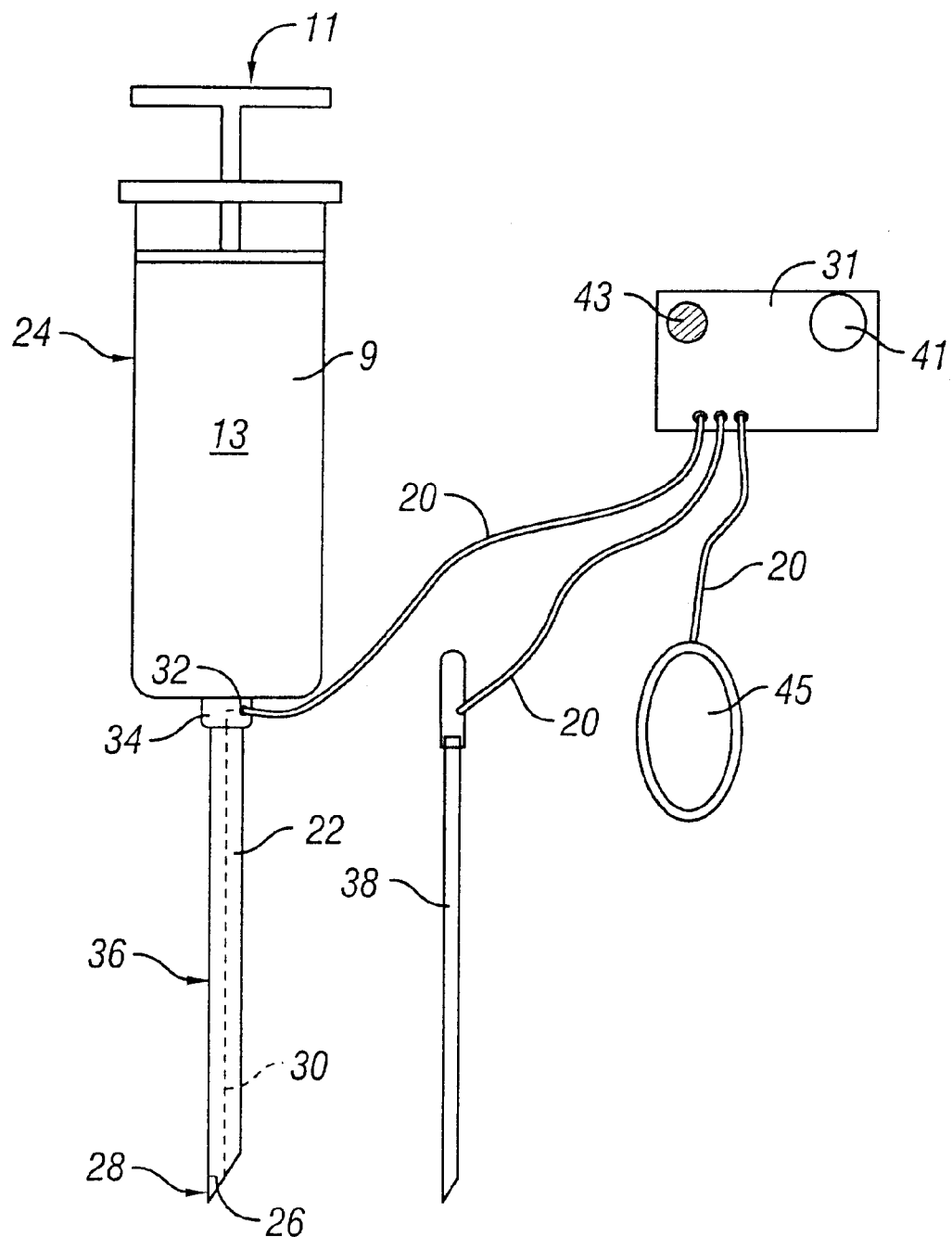
FIG. 4 is a front elevation view of an EMG needle-injection device, according to a third embodiment.

In a third embodiment 24, on a needle/electrode/syringe unit 36, as shown in FIG. 4, an electrically conducting needle 22 is insulated along its entire length except for an uninsulated portion 26 at the sharpened tip 28. The needle 22 provides the electrical connection 30 between the uninsulated portion 26 and the connection point 32, although it has no exposed conductive surfaces in between the connection point 32 on the needle hub 34 and the uninsulated portion 26. The uninsulated portion 26 of the needle 22 serves as a trigger point electrode. The trigger point electrode is thereby connected to an analyzer 31 via a cable 20. An adjacent muscle electrode 38 in the form of a needle, and a reference skin patch electrode 45 are separately provided and linked to the analyzer 31 by cables 20. In use, the reference skin patch electrode 45 is applied to the skin and the respective trigger point and muscle electrodes 26 and 38 are separately placed. When trigger point EMG activity is detected, as described above, a drug is injected at the trigger point, using the syringe on the device 24.

Figure 7:
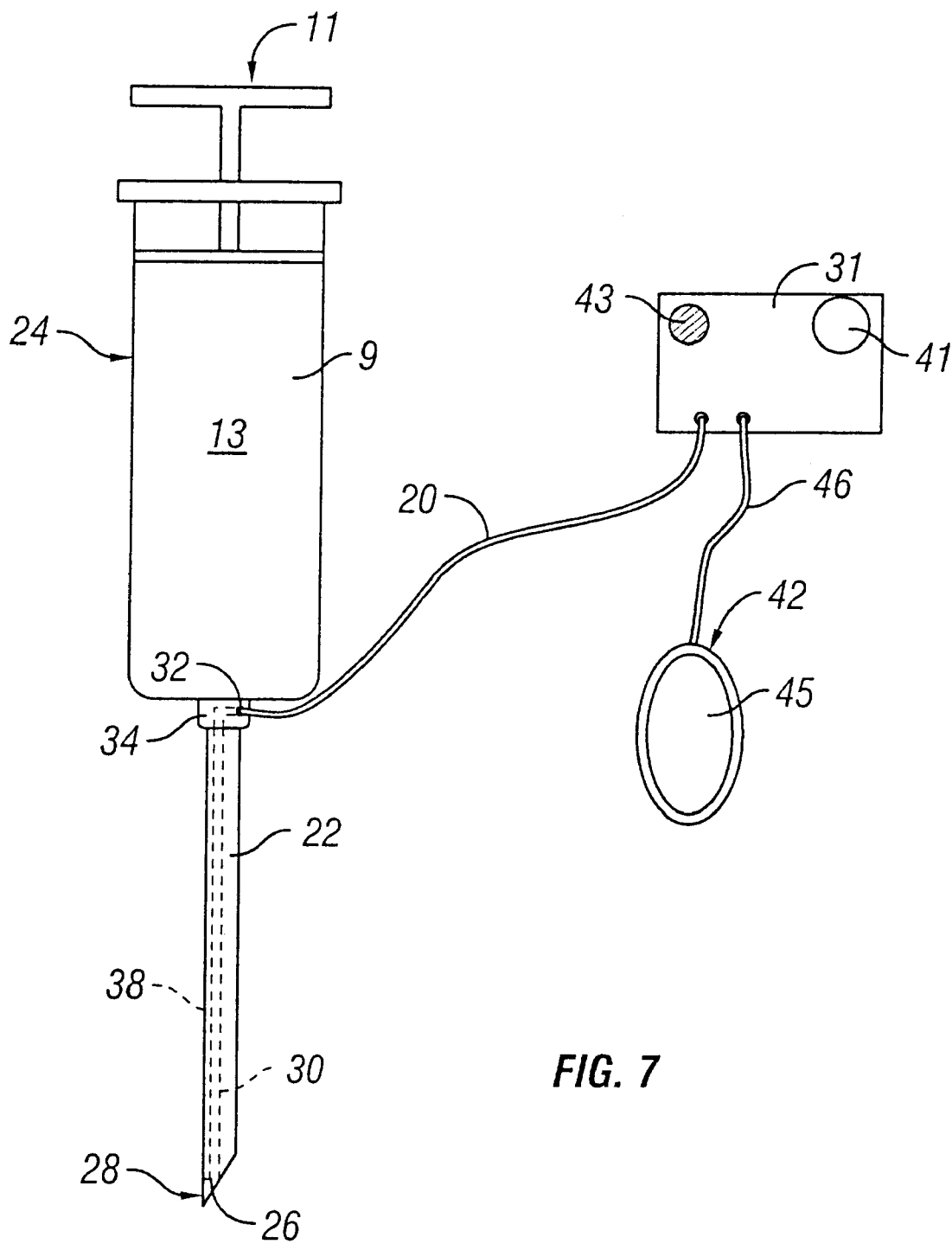
FIG. 7 is a front elevation view of an EMG injection device, according to a fourth embodiment.

FIG. 7 shows a fourth embodiment similar to FIG. 4, but having the trigger point electrode 26 and the adjacent muscle electrode 38 on the needle 22. Both electrodes 26 and 38 are connected via a cable 20 to an analyzer 31. The reference electrode 42 is provided as skin patch 45 connected to the analyzer 31 by a cable 46.

Thus, while several embodiments have been shown and described, various modifications may be made without departing from the spirit and scope of the invention. The invention, therefore, should not be restricted, except by the following claims.

What is claimed is:

1. A device for diagnosis or treatment of muscle pain comprising:
   a needle;
   a trigger point electrode on the needle;
   at least one adjacent electrode on the needle spaced apart from the trigger point electrode;
   a reference electrode; and
   an analyzer linked to the trigger point electrode, the at least one adjacent electrode, and the reference electrode wherein the analyzer detects activity at the trigger point electrode that is detectively more than activity detected at the at least one adjacent electrode.

2. The device of claim 1 further comprising means for delivering a drug.

3. The device of claim 2 wherein the means for delivering further comprises a syringe attached to the needle.

4. The device of claim 3 wherein the syringe and the needle are separable.

5. The device of claim 3 further comprising a holder including electrical contacts for connecting with the trigger point electrode, the at least one adjacent electrode, and the reference electrode.

6. The device of claim 5 wherein the holder is reusable, and wherein the trigger point electrode, the at least one adjacent electrode, the reference electrode, the syringe, and the needle are disposable.

7. The device of claim 1 wherein the reference electrode is disposed on the needle.

8. The device of claim 1 wherein the trigger point electrode is spaced vertically apart from the at least one adjacent electrode.

9. A system for diagnosing or treating muscle pain, comprising:
   an EMG device including a trigger point electrode, at least one adjacent electrode, and a reference electrode on a hypodermic needle;
   a holder having electrical contacts for connecting to the electrodes; and
   an analyzer connected to the trigger point, adjacent and reference electrodes via the contacts in the holder, for detecting EMG activity at the trigger point electrode that is detectively more than EMG activity detected at the at least one adjacent electrode.

10. The system of claim 9 wherein the trigger point electrode and the at least one adjacent electrode are spaced apart sufficiently for identifying EMG activity localized to a trigger point.

11. The system of claim 9 further comprising means for delivering a drug.

12. The system of claim 9 wherein the trigger point electrode and the at least one adjacent electrode are vertically spaced apart by about 2–4 mm.

13. The system of claim 9 further comprising a drug holding vessel attached to the needle.

14. The system of claim 13 wherein the drug holding vessel further comprises a syringe.

15. The system of claim 9 wherein the electrodes comprise electrically conductive elements.

16. The system of claim 9 wherein the trigger point electrode is at a sharp tip on the needle.

17. The system of claim 9 further comprising means for alerting a physician when spontaneous EMG activity at a trigger point exceeds EMG activity in adjacent muscle tissue by a predetermined amount.

18. The system of claim 9 further comprising a display for visually displaying EMG input signals from the electrodes.

19. The system of claim 9 further comprising an audio system for communicating EMG activity signals via sound.

20. A device for diagnosing or treating muscle pain comprising:
   a delivery system including a vessel for holding a drug;
   an electrically conductive hypodermic needle insulated along its entire length except for an uninsulated section at a sharp tip of the needle forming a trigger point electrode;
   an adjacent muscle electrode;
   a reference electrode; and
   an analyzer linked to the trigger point, adjacent muscle, and reference electrodes, wherein the trigger point, adjacent muscle and reference electrodes are separate from each other such that the analyzer detects muscle pain activity at the trigger point electrode that is detectively more than activity detected at the adjacent muscle electrode.

21. The device of claim 20, wherein the adjacent muscle electrode is separate from the hypodermic needle.

22. The device of claim 20, wherein the reference electrode comprises a skin patch electrode separately provided from the needle.

23. The device of claim 20, wherein the adjacent muscle electrode is disposed on the hypodermic needle.

24. A device for diagnosis or treatment of muscle pain comprising:
- a needle;
- a trigger point electrode disposed on the needle;
- at least one adjacent electrode spaced apart from the trigger point electrode;
- a reference electrode; and
- an analyzer linked to the trigger point, adjacent, and reference electrodes wherein the analyzer detects activity at the trigger point electrode that is substantially more than activity detected at the at least one adjacent electrode.

25. The device of claim 24 further comprising means for delivering a drug.

26. The device of claim 25 wherein the means for delivering further comprises a syringe attached to the needle.

27. The device of claim 24 wherein the trigger point electrode is spaced vertically apart from the at least one adjacent electrode.

28. The device of claim 24 wherein the reference electrode is disposed on the needle.

29. The device of claim 24 further comprising a holder including electrical contacts for connecting with the electrodes.

30. The device of claim 29 wherein the holder is reusable, and the electrodes and the needle are disposable.

31. The device of claim 24, wherein the at least one adjacent electrode is separate from the needle.

32. The device of claim 24, wherein the reference electrode comprises a skin patch electrode separately provided from the needle.

33. The device of claim 24, wherein the at least one adjacent electrode is disposed on the needle.

34. A method for diagnosing and treating muscle pain comprising the steps of:
- providing an electrically conductive needle insulated along its entire shaft except for an uninsulated section at a sharp tip of the needle forming a trigger point electrode;
- placing an adjacent muscle electrode separately from the trigger point electrode;
- applying a reference electrode to a patient's skin;
- linking an analyzer to the trigger point electrode, the adjacent muscle electrode and the reference electrode;
- detecting muscle pain activity at the trigger point electrode that is substantially more than activity detected at the adjacent muscle electrode; and
- when muscle pain activity is detected, injecting a drug at the trigger point electrode.

35. The method of claim 34, wherein the step of placing an adjacent muscle electrode further comprises placing the adjacent muscle electrode separate from the needle.

36. The method of claim 34 wherein the step of placing an adjacent muscle electrode further comprises laying the adjacent muscle electrode along the shaft of the needle.

* * * * *